United States Patent
Yoshizaki et al.

(10) Patent No.: US 10,590,320 B2
(45) Date of Patent: Mar. 17, 2020

(54) ADHESIVE MOLECULES

(71) Applicants: THE CHUGOKU ELECTRIC POWER CO., INC., Hiroshima (JP); SESSILE RESEARCH CORPORATION, Hyogo (JP)

(72) Inventors: Tsukasa Yoshizaki, Hiroshima (JP); Keiji Yamashita, Hyogo (JP); Kyoko Kamiya, Hyogo (JP); Kohichi Suzuki, Hyogo (JP); Yoshio Hayashi, Hyogo (JP)

(73) Assignees: THE CHUGOKU ELECTRIC POWER CO., INC., Hiroshima (JP); SESSILE RESEARCH CORPORATION, Hyogo (JP)

(*) Notice: Subject to any disclaimer, the term of this patent is extended or adjusted under 35 U.S.C. 154(b) by 176 days.

(21) Appl. No.: 15/561,194

(22) PCT Filed: Mar. 23, 2015

(86) PCT No.: PCT/JP2015/058771
§ 371 (c)(1),
(2) Date: Dec. 4, 2017

(87) PCT Pub. No.: WO2016/151736
PCT Pub. Date: Sep. 29, 2016

(65) Prior Publication Data
US 2018/0362817 A1    Dec. 20, 2018

(51) Int. Cl.
| | |
|---|---|
| C09J 189/00 | (2006.01) |
| C07K 7/08 | (2006.01) |
| A61L 24/00 | (2006.01) |
| C12N 15/09 | (2006.01) |
| A61K 38/00 | (2006.01) |
| C08K 5/16 | (2006.01) |
| C12N 15/62 | (2006.01) |

(52) U.S. Cl.
CPC .............. *C09J 189/00* (2013.01); *A61K 38/00* (2013.01); *A61L 24/00* (2013.01); *C07K 7/08* (2013.01); *C08K 5/16* (2013.01); *C12N 15/09* (2013.01); *C12N 15/62* (2013.01)

(58) Field of Classification Search
None
See application file for complete search history.

(56) References Cited

U.S. PATENT DOCUMENTS

2009/0151600 A1    6/2009   Cha et al.
2011/0033891 A1*   2/2011   Cha .................. C07K 14/43504
                                                       435/69.1

FOREIGN PATENT DOCUMENTS

| JP | H08-266282 A | 10/1996 |
| JP | 2008-504016 A | 2/2008 |
| JP | 2013-226158 A | 11/2013 |

OTHER PUBLICATIONS

Bowie et al., "Deciphering the message in protein sequences: tolerance to amino acid substitutions," Science. 247(4948):1306-1310 (1990) (8 pages).
Dalbadie-McFarland et al., "Oligonucleotide-directed mutagenesis as a general and powerful method for studies of protein function," Proc. Natl. Acad. Sci. USA. 79(21):6409-6413 (1982).
Fukuda et al., "Molecular cloning of a cDNA encoding a soluble protein in the coral exoskeleton," Biochemical and Biophysical Research Communications. 304(1):11-17 (2003) (13 pages).
Mark et al., "Site-specific mutagenesis of the human fibroblast interferon gene," Proc. Natl. Acad. Sci. USA. 81(18):5662-5666 (1984).
International Search Report for International Application No. PCT/JP2015/058771, dated May 19, 2015 (English language translation provided) (5 pages).
Written Opinion of the International Searching Authority for International Application No. PCT/JP2015/058771, dated May 19, 2015 (English language translation provided) (7 pages).
International Preliminary Report on Patentability for International Application No. PCT/JP2015/058771, dated Sep. 26, 2017 (English language translation provided) (9 pages).
Extended European Search Report for European Patent Application 15886291.2 dated Aug. 7, 2018 (5 pages).
Wilke et al., A direct biocombinatorial strategy toward next generation, mussel-glue inspired saltwater adhesives, J Am Chem Soc. 136(36):12667-74 (2014).

* cited by examiner

*Primary Examiner* — Christina Bradley
(74) *Attorney, Agent, or Firm* — Clark & Elbing LLP

(57) ABSTRACT

To provide novel adhesive molecules. An adhesive molecule having an amino acid sequence of SEQ ID NO. 1, or an amino acid sequence including a conservative substitution, a deletion, an insertion and/or a modification in the sequence of SEQ ID NO. 1.

13 Claims, 4 Drawing Sheets

Specification includes a Sequence Listing.

[Fig. 1]
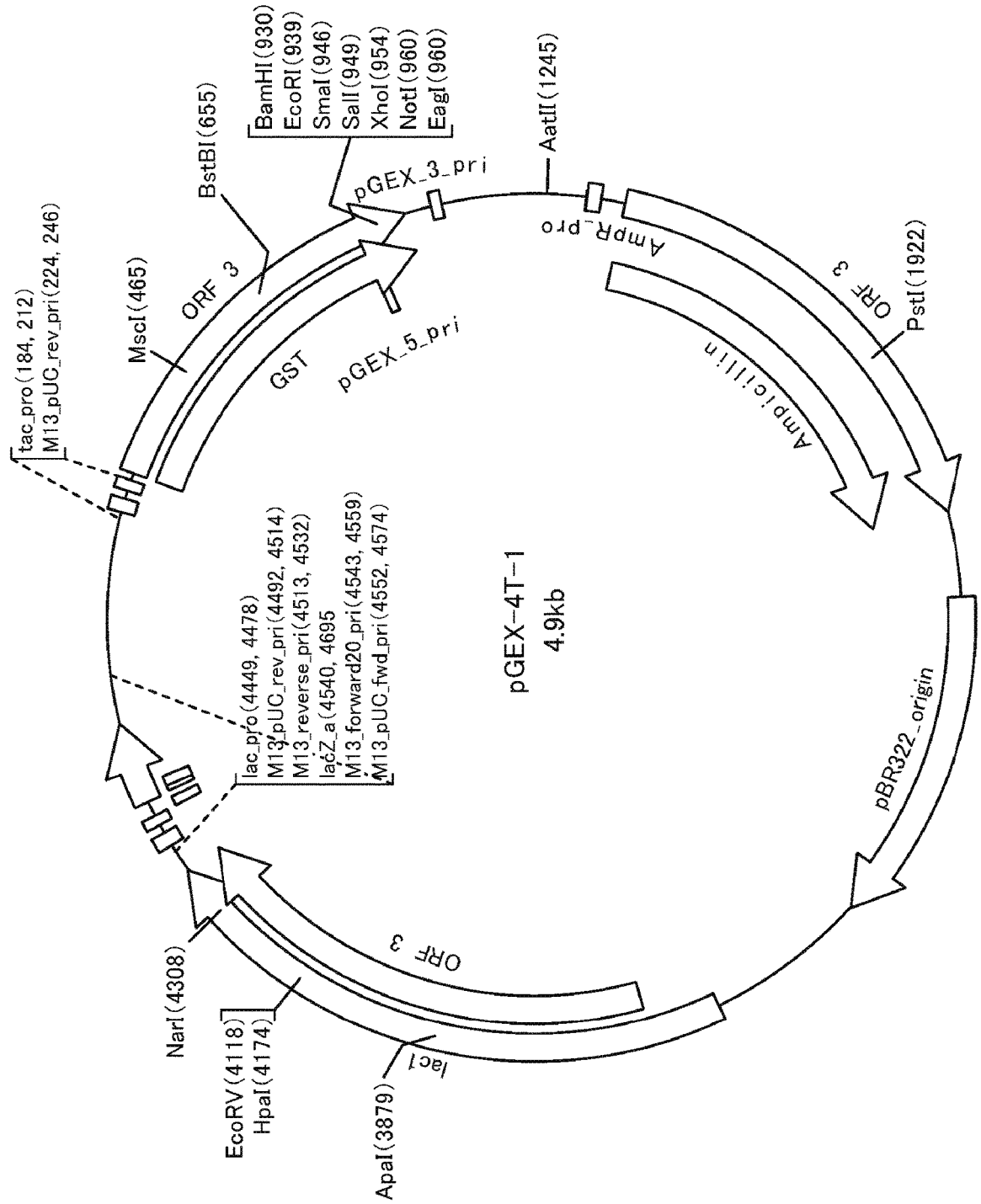

[Fig. 2]
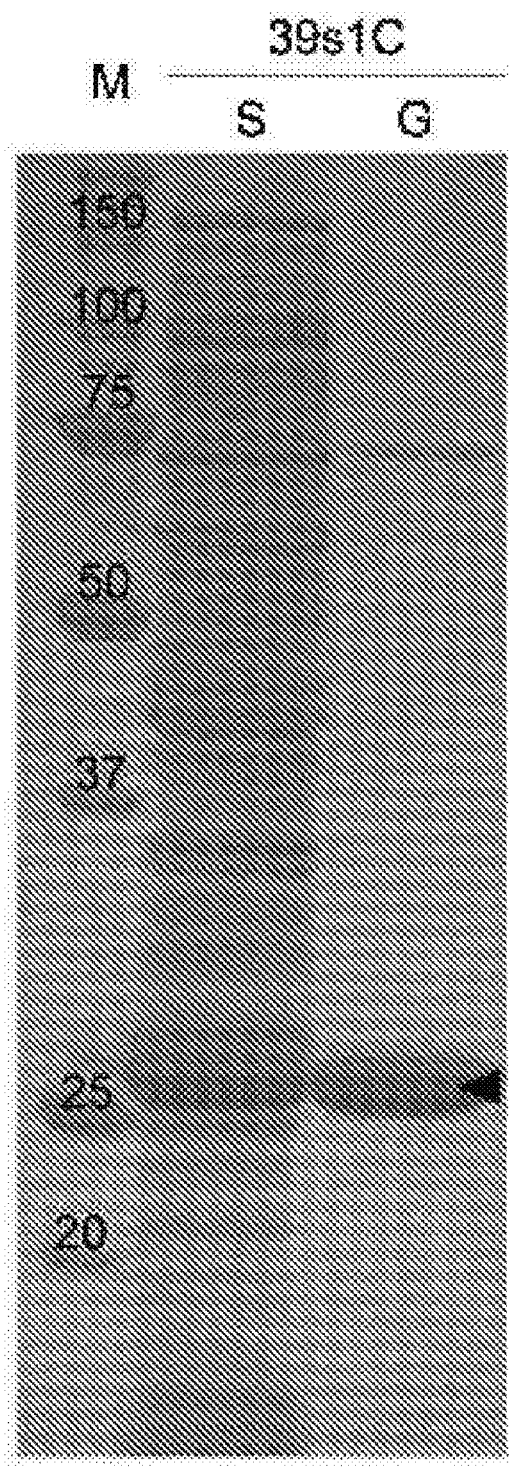
M: Marker
S: Soluble fraction
G: Purified GST Product
GST+(39s1C)≈28.33kDa

[Fig. 4]
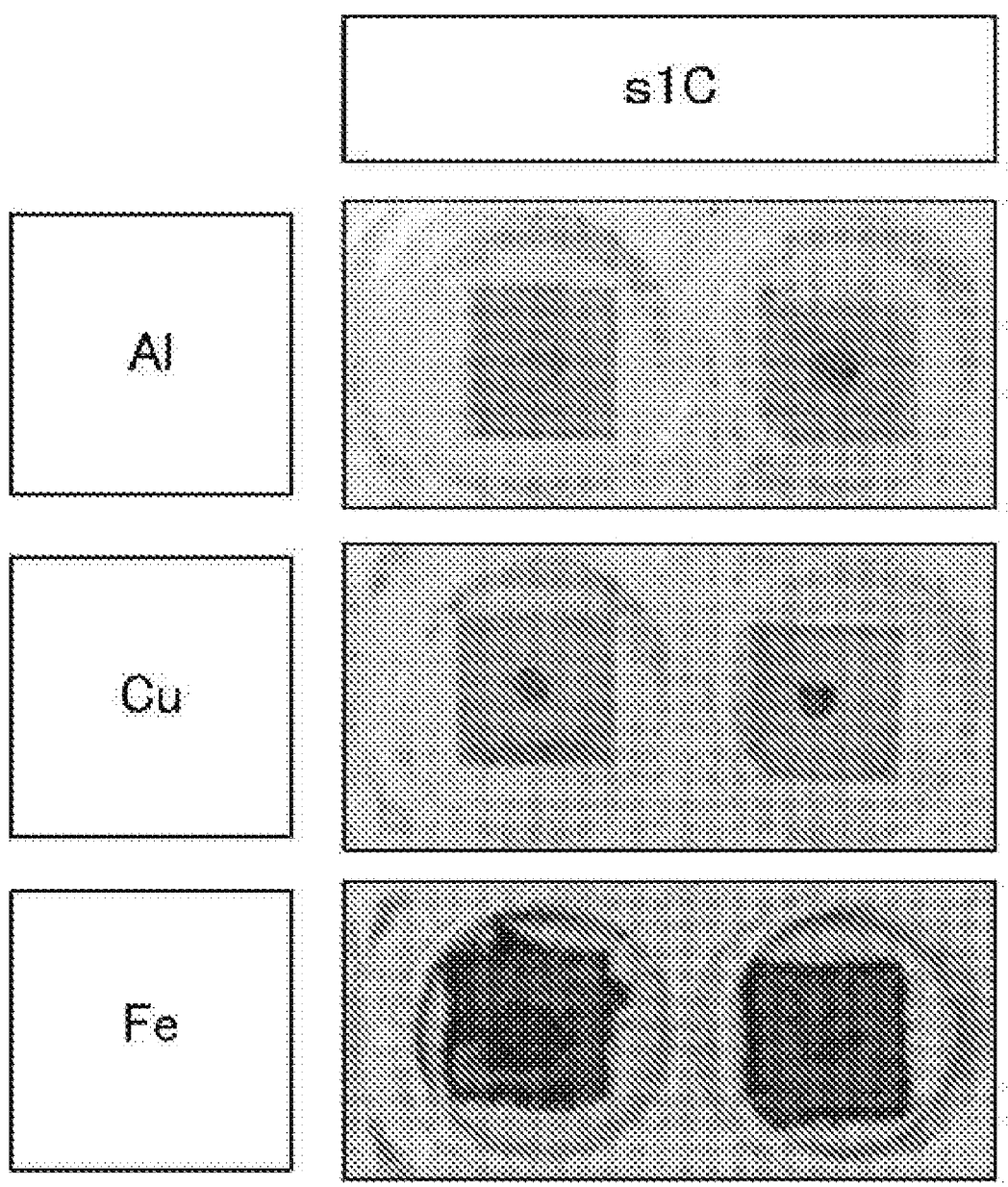

ADHESIVE MOLECULES

TECHNICAL FIELD

The present invention relates to adhesive molecules.

BACKGROUND ART

As underwater adhesive molecules derived from organisms, adhesive proteins derived from marine organisms, Balanomorpha and Mytilidae, are disclosed (see, for example, Patent Documents 1 to 3). Adhesive proteins derived from Balanomorpha, however, have not been practically used due to complicated production process that involves, for example, mixing 6 to 8 kinds of proteins to achieve adherence. On the other hand, adhesive proteins derived from Mytilidae are commercially available as bioadhesives containing three kinds of adhesive proteins under the trade name Cell-Tak™, but these proteins are difficult to go into mass production and are thus expensive. Accordingly, discovery of novel adhesive molecules has been awaited.

RELATED ART DOCUMENTS

Patent Documents

Patent Document 1: JP-A-8-266282
Patent Document 2: JP-A-2013-226158
Patent Document 3: JP-A-2008-504016

SUMMARY OF THE INVENTION

Problems to be Solved by the Invention

An object of the present invention is to provide novel adhesive molecules.

Means to Solve the Problems

The present inventors found a protein showing 37% homology with galaxin in peptides that are specifically present in the cement gland of actinula larvae of *Tubularia* sp. Investigations of properties of this newly discovered protein led to the findings that a peptide having a sequence of SEQ ID NO. 1 obtained by replacing a part of 18 amino acids at its C-terminus had adherence and then the present invention was completed. It should be noted that galaxin is a protein supposed to be involved in the calcification mechanism by which coral skeletons are formed in *Galaxea fascicularis* (see, for example, Fukuda et al., Biochem. Biophys. Res. Commun. 2003 Apr. 25; 304(1):11-7) but information related to adherence have not been reported so far on the protein.

An aspect of the present invention is an adhesive molecule having an amino acid sequence of SEQ ID NO. 1, or an amino acid sequence of SEQ ID NO. 1 having a conservative amino acid substitution, a deletion, an insertion and/or a modification. The adhesive molecule may contain at least one dihydroxyphenylalanine.

Another aspect of the present invention is an adhesive containing the aforementioned adhesive molecule.

A yet another aspect of the present invention is a polynucleotide having a nucleotide sequence encoding the aforementioned adhesive molecule.

A yet another aspect of the present invention is a vector having the polynucleotide having a nucleotide sequence encoding the aforementioned adhesive molecule.

A still another aspect of the present invention is a method of bonding a first object to a second object, including applying the aforementioned adhesive to a surface of the first object.

A still another aspect of the present invention is a method of coating a surface of an object including applying the adhesive to the surface of the object.

A still another aspect of the present invention is a method of enhancing adherence of an adhesive molecule including reacting tyrosinase with the aforementioned adhesive molecule.

Effect of the Invention

The present invention made it possible to provide novel adhesive molecules.

BRIEF DESCRIPTION OF THE DRAWINGS

FIG. 1 shows a map of the vector pGEX4T-1 which is used to produce adhesive molecules in microorganisms, according to an embodiment of the present invention.

FIG. 2 shows a result of SDS-PAGE of a GST-recombinant peptide fusion product produced in *E. coli*, according to an embodiment of the present invention.

FIG. 4 shows adherence of adhesive molecules according to an embodiment of the present invention.

EMBODIMENTS FOR CARRYING OUT THE INVENTION

Figure 3A:
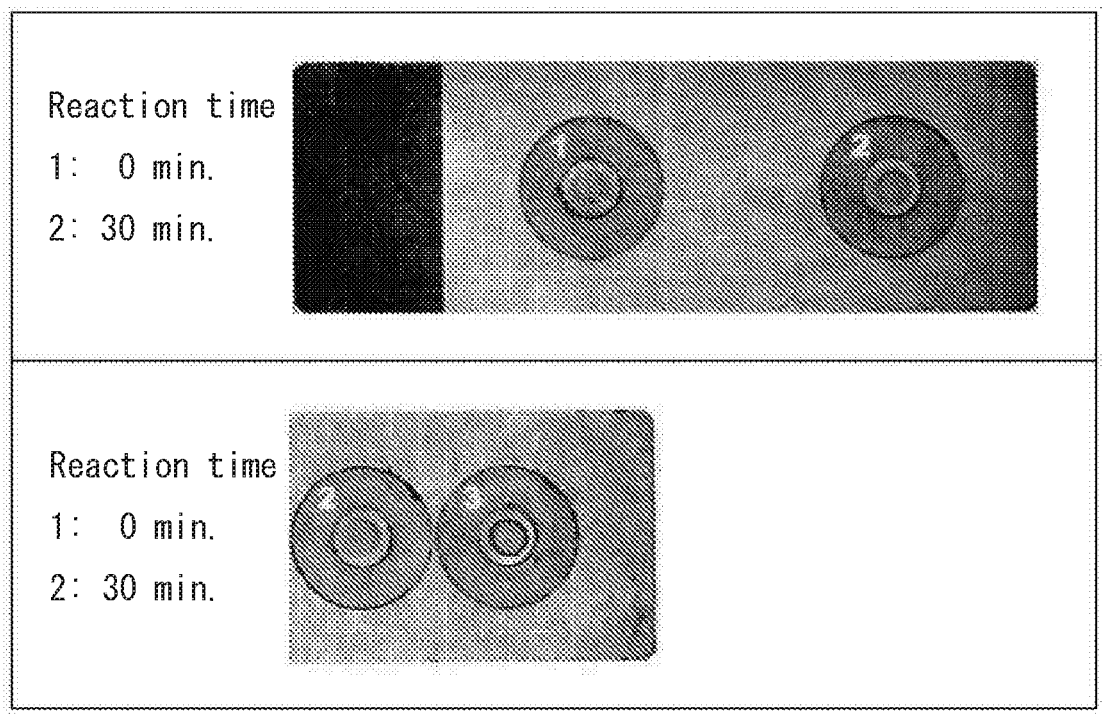
FIG. 3A and Fig.3B shows views illustrating adherence of adhesive molecules according to an embodiment of the present invention.

Embodiments of the present invention are described in detail along with examples.

Unless otherwise noted in embodiments and examples, all procedures used are according to standard protocols described in, for example, J. Sambrook, E. F. Fritsch & T. Maniatis (Ed.), Molecular cloning, a laboratory manual (3rd edition), Cold Spring Harbor Press, Cold Spring Harbor, N.Y. (2001); F. M. Ausubel, R. Brent, R. E. Kingston, D. D. Moore, J. G. Seidman, J. A. Smith, K. Struhl (Ed.), Current Protocols in Molecular Biology, John Wiley & Sons Ltd., with or without modifications or changes. In addition, commercial reagent kits or measurement instruments are used as described in protocols attached thereto, unless otherwise noted.

The objects, features, advantages, and ideas of the present invention are apparent to those skilled in the art from the description of this specification. Furthermore, those skilled in the art can easily reproduce the present invention from the description herein. The embodiments and specific examples described below represent preferable embodiments of the present invention, which are given for the purpose of illustration or explanation. The present invention is not limited thereto. It is obvious to those skilled in the art that various changes and modifications may be made according to the description of the present specification within the spirit and scope of the present invention disclosed herein.

(1) Adhesive Molecules of the Present Invention

Adhesive molecules of the present invention have a sequence NRVDNYKEVYNKIYNKRN (SEQ ID NO. 1), or a sequence of SEQ ID NO. 1 having conservative amino acid substitutions, deletions, insertions and/or modifications. In the present invention, "conservative amino acid substitutions, deletions, insertions and/or modifications" means substitutions, deletions, insertions and/or modifications that do not impair properties of peptide, that is, do not impair adherence of the adhesive molecules. The adherence as used herein refers to a character of adhering to and settling on a surface of an object without being separated from the surface of the object even after the object is washed, and a molecule is judged to have adherence when a blue band was observed in a test described in Example 2. With such adherence, two objects can be adhered and joined to each other by bonding the two objects to an adherent substance simultaneously.

Examples of a conservative amino acid substitution of the present invention include substitutions of an amino acid with another in the same group categorized according to, for example, bulk, polarity, hydrophobicity or hydrophilicity, and acidity or basicity of amino acid residues. Examples of categories are well known to persons skilled in the art and described in various documents (see, for example, Bowie et al., Science, 247:1306-1310 (1990) and Zubay, G., Biochemistry, third edition, Wm. C. Brown Publishers (1993)). For example, amino acids for conservative substitution can be selected based on the groups of amino acids exemplified below. The letters in the parentheses are abbreviations for amino acids in the three letter format.

Hydrophobic amino acids (Ala, Ile, Leu, Met, Phe, Pro, Trp, Tyr, and Val)
Hydrophilic amino acids (Arg, Asp, Asn, Cys, Glu, Gln, Gly, His, Lys, Ser, and Thr)
Amino acids with side chains containing aromatic rings (His, Phe, Tyr, and Trp)
Amino acids with aliphatic side chains (Gly, Ala, Val, Leu, Ile, and Pro)
Amino acids with side chains containing hydroxyl groups (Ser, Thr, and Tyr)
Amino acids with side chains containing sulfur atoms (Cys and Met)
Amino acids with side chains containing amides and carboxylic acids (Asp, Asn, Glu, and Gln)
Amino acids containing acidic groups (Asp and Glu)
Amino acids containing basic groups (Arg, Lys, and His)
Polar amino acids (Gln and Asn)
Non-polar amino acids (Gly, Ala, Phe, Val, Leu, Ile, Met, Pro, and Trp)
Amino acids with small side chains (Gly, Ala, Ser, Thr, and Met)
Amino acids with β-branched side chains (Thr, Val, and Ile)

It is also known in the art that peptides having an amino acid sequence including a substitution, a deletion, an insertion and/or a modification of one to several amino acid residues relative to a certain amino acid sequence do not lose their properties (see, for example, Mark, D. F. et al., Proc. Natl. Acad. Sci. USA (1984) 81, 5662-5666, and Dalbadie-McFarland, G. et al., Proc. Natl. Acad. Sci. USA (1982) 79, 6409-6413).

The number of conservative amino acid substitutions, deletions, insertions and/or modifications is not particularly limited as long as the adherence of the adhesive molecules are not impaired, and the number for each may be any number equal to or larger than 1. The number for each is preferably 4 or smaller, more preferably 3 or smaller, yet more preferably 2 or smaller, and most preferably 1 or smaller.

It is preferable that the adhesive molecule of the present invention has the sequence of NRVDNYKEVYNKI-YNKRN (SEQ ID NO. 1).

It is preferable that the adhesive molecules of the present invention have at least one modified tyrosine residue, dihydroxyphenylalanine (hereinafter, referred to as "DOPA"). In DOPA, the hydrogen atom at position 3 of the benzene ring of the tyrosine residue is replaced with a hydroxyl group. The number of DOPAs contained in an adhesive molecule of the present invention is not particularly limited, but more preferably two, and yet more preferably three. A method of converting a tyrosine residue into DOPA is not particularly limited. For example, molecules having capability of replacement with a hydroxyl group, addition of an oxygen, oxidization can be used. It is preferable that tyrosinase is used.

(2) Method of Producing Adhesive Molecules of the Present Invention

A method of producing adhesive molecules of the present invention is not particularly limited and methods of synthesizing them chemically or producing them in cells are examples.

Examples of chemical synthesis include solid phase peptide synthesis such as Boc or Fmoc strategies and liquid phase peptide synthesis, but not limited thereto. It is generally understood that rather shorter peptides can be synthesized more easily and the adhesive molecules of the present invention have a length that allows their easy synthesis.

In a method of producing adhesive molecules in cells, an expression vector, which has a nucleotide sequence encoding an amino acid sequence of an adhesive molecule of the present invention and can express the adhesive molecule, is constructed and introduced into cells to make transformants; and the transformants are allowed to produce the adhesive molecule of the present invention. Methods of constructing an expression vector, introducing it into cells, allowing the cells to produce the protein are known to persons skilled in the art and can be achieved using any one of available methods. The cells are not limited and examples include yeast, insect cells, plant cells, animal cells, and microorganisms. E. coli is typically used. The adhesive molecules of the present invention produced in cells can be recovered from the cells or a medium in which the cells have been cultured and then purified using any one of the methods known to persons skilled in the art. The purified adhesive molecules of the present invention can be stored in any methods such as freezing or freeze-drying.

Furthermore, in producing adhesive molecules of the present invention, adherence of adhesive molecules of the present invention may be enhanced under a reaction condition used to convert a tyrosine residue into DOPA, for example, by reacting a tyrosine residue with tyrosinase. In order to achieve a desired adherence, a period of the reaction with tyrosinase can appropriately be determined. The reaction time is not particularly limited but is preferably 10 minutes or longer, more preferably 30 minutes or longer, and yet more preferably 60 minutes or longer.

(3) Applications of Adhesive Molecules of the Present Invention

The adhesive molecules of the present invention can be used as an active ingredient of an adhesive used to bond objects to each other. The objects to be bonded are not particularly limited and examples include glass, polymer compounds such as plastics and resins, metals, woods, or biomaterials. Either objects of the same kind or objects of different kinds can be bonded to each other.

Other component(s) in the adhesive containing the adhesive molecules of the present invention can appropriately be selected to impart, to the adhesive, a desired adhesive strength or a character suitable for an environment where the adhesive is to be used, and vehicles are typical examples. Examples of vehicles include known surfactants, oxidants, and fillers. As alternative examples, known adhesive molecules can be contained.

The concentration of the adhesive molecules of the present invention in the adhesive is not particularly limited and can appropriately be selected from, for example, 1 to 99% (w/v), 5 to 95% (w/v), 10 to 90% (w/v), 20 to 80% (w/v), 30 to 70% (w/v), and 40 to 60% (w/v). The concentration of the adhesive molecules is preferably 0.001% or higher (w/v), and more preferably 0.01% or higher (w/v). The form of the adhesive is not particularly limited and may be either in a liquid form or in a solid form. Examples include adhesives in the form of liquid, mist, or gel and adhesive tapes.

The environment where the adhesive molecules of the present invention and/or adhesives made of the adhesive molecules are used is not particularly limited, and an underwater environment (in freshwater or in salt water) or an environment within a living body are examples. For example, they can be used as an underwater adhesive in a civil engineering field, as a dental adhesive (also called an adhesive resin cement) or a hemostatic agent in a living body in a medical field, and as a reagent for regenerative medicine or a component thereof.

The adhesive molecules according to the present invention can be used as a coating agent taking advantage of their character of adhering to a surface of an object. This coating agent imparts adherence to the surface of the object and therefore give character of capturing of moving things (such as microparticles, microorganisms, and large or small organisms) to the object. Since the adhesive molecules of the present invention are not taken off from the surface even by washing, an object can be used as a trap for taking, for example, marine organisms by coating it with the adhesive molecules in water.

(4) Methods of Bonding and Coating Using Adhesive Molecules of the Present Invention Objects can be bonded using an adhesive containing adhesive molecules of the present invention. For example, objects can be bonded to each other by applying an adhesive of the present invention to a surface of an object using any method such as instillation or coating, placing another object on top of it, and drying it. The amount of the adhesive used for bonding can appropriately be determined depending on a purpose.

As an example of a method of coating a surface of an object using an adhesive containing adhesive molecules of the present invention, the adhesive containing a certain concentration of the adhesive molecules of the present invention can be applied to the surface of the object using any method such as instillation or coating and appropriately be dried.

In methods of bonding and coating, a drying period is not particularly limited but is preferably 5 minutes or longer, more preferably 10 minutes or longer, yet more preferably 30 minutes or longer, and most preferably 60 minutes or longer. Depending on a surface area to be bonded or coated, drying may be performed for a longer period of time.

EXAMPLES

Example 1

Production of Adhesive Molecules Using *E. coli*

An non-natural polynucleotide (SEQ ID NO. 2) was created by determining a nucleotide sequence corresponding to the amino acid sequence of SEQ ID NO. 1 and adding recognition sequences for the restriction enzyme BamHI to the both ends of the nucleotide sequence.

The vector pGEX4T-1 (Merck Millipore) shown in FIG. 1 was digested with the aforementioned restriction enzymes and ligated to the non-natural polynucleotide. A nucleotide sequence generated by insertion of the non-natural polynucleotide into the vector was determined using a sequencing technique. This vector was introduced into a host *E. coli* BL21, GE Healthcare) according to the attached protocol to generate a transformant. The vector pGEX4T-1 is formed so that the N-terminus of a peptide to be expressed is fused to Glutathione S-transferase (GST).

The transformant obtained was cultured with shaking at 37° C. in an LB medium supplemented with ampicillin at a final concentration of 50 µg/ml. When the turbidity (OD600) of the medium reached 0.4 to 0.8, isopropyl-β-thiogalactopyranoside (isopropyl β-D-1-thiogalactopyranoside, IPTG) was added to the LB medium at a final concentration of 0.1 mM to induce expression of the GST-fused recombinant peptide. After the addition of IPTG, the culture with shaking was continued at 37° C. for 3 hours until the turbidity of the LB medium became steady, that is, the growth of *E. coli* became steady. The culture condition of incubation at an IPTG concentration of 0.1 mM at a temperature of 37° C. for 3 hours was determined so that the GST-fused recombinant peptide was soluble in a soluble fraction described below.

Next, the medium with the transformants was centrifuged (6,000 rpm at 4° C.) to remove the supernatant and the precipitates were resuspended in phosphate buffered saline (PBS) to obtain PBS suspension. The PBS suspension was subjected to ultrasonic disruption and then centrifuged at 12,000 rpm and 4° C. for 5 minutes to collect the supernatant. The supernatant is a soluble fraction in which the GST-fused recombinant peptide is present. This soluble fraction was mixed with Glutathione Sepharose 4B beads (GE Healthcare) and the GST-fused recombinant peptide was allowed to bind to the beads. The binding was carried out according to the protocol attached to the beads. The beads to which the GST-recombinant peptide fusion products were bound was washed several times with PBS and then mixed with PBS in which thrombin had been dissolved. The mixture was incubated at room temperature (22 to 25° C.) for 2 to 16 hours to cleave the recombinant peptides from GST. Next, this mixture was centrifuged (at 5,000 g and 4° C. for 5 minutes) to reover the supernatant. The supernatant contained the recombinant peptide and thrombin and the latter was removed using a benzamidine column (a column for purification and removal of serine protease, GE Healthcare). The recovered recombinant peptide is hereinafter referred to as 39 slC. Expression of the GST-fused recombinant peptide in the transformants was confirmed using SDS-PAGE shown in FIG. 2. A signal for the GST-fused recombinant peptide is indicated by a black arrow.

Example 2

Test for Adherence of Adhesive Molecules of the Present Invention to Glass

Two different peptide solutions were prepared: a peptide solution of purified 39 slC obtained by mixing with purified water and a peptide solution of BSA obtained by dissolving in purified water. The concentration of peptides was 1 mg/ml for both. 1 µl of the peptide solutions were each added dropwise onto a glass slide. Next, 1 µl of tyrosinase solution (1 mg/ml) prepared by dissolving lyophilized tyrosinase in potassium phosphate buffer (50 mM, pH6.5) was added to the dripped peptide solutions and gently mixed by pipetting. The glass slides were placed statically in an atmosphere of saturated water vapor at 22 to 25° C. and incubated for 0 or 30 minutes. After the incubation, they were dried under vacuum at room temperature. Subsequently, the glass slides were washed for 30 minutes with shaking at 45 times/min. in distilled water. Then, they were dried under vacuum at room temperature again. After the drying, the glass slides were immersed in a 0.25% CBB (R-250) solution overnight and were then washed several times with distilled water. It was visually examined whether blue staining with the CBB staining was observed on the slides. If the peptide is bound to the surface of the glass, blue staining with the CBB staining should be observed.

Figure 3B:
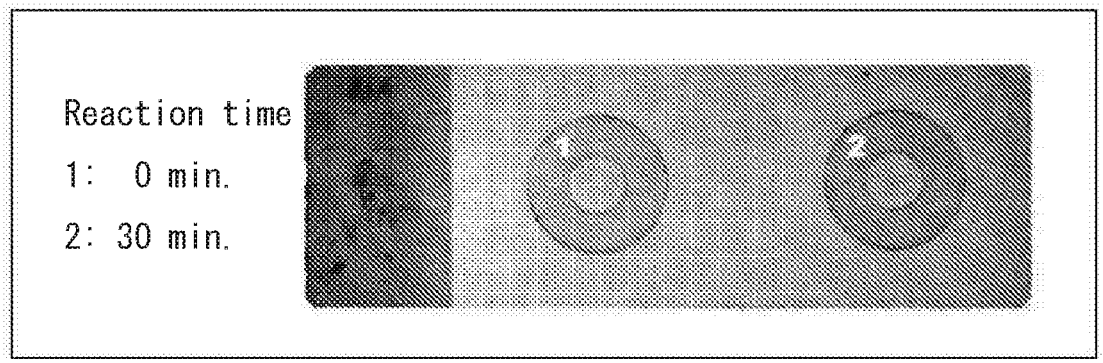

As shown in FIG. 3, BSA of both reaction time of 0 and 30 minutes was not attached to the glass slide after the 30-minute washing (FIG. 3(B)). On the contrary, blue staining indicating that the 39 slC of both reaction time of 0 and 30 minutes was attached to the glass slide was observed even after the 30-minute washing, and stronger blue staining was observed after 39 slC and tyrosinase were incubated for 30 minutes to convert tyrosine residues to DOPA, indicating that more peptides were bound to the glass slide (FIG. 3(A)).

Example 3

Test for Adherence of Adhesive Molecules of the Present Invention to Metal

A peptide solution was prepared by mixing purified 39 slC and purified water. The concentration of the peptide was 1 mg/ml. 1 μl of the peptide solution was added dropwise onto surfaces of an aluminum (Al) plate, a copper (Cu) plate and an iron (Fe) plate. Next, 1 μl of tyrosinase solution (1 mg/ml, prepared by dissolving lyophilized tyrosinase in potassium phosphate buffer (50 mM, pH6.5)) was added and gently mixed by pipetting. The glass slides were placed statically in an atmosphere of saturated water vapor at 22 to 25° C. and incubated for 30 minutes. After the incubation, they were dried under vacuum at room temperature. Subsequently, the glass slides were washed for 30 minutes with shaking at 45 times/min. in distilled water. Then, they were dried under vacuum at room temperature again. After drying, the glass slides were immersed in a 0.25% CBB (R-250) solution overnight and were then washed several times with distilled water. It was visually examined whether blue staining by the CBB is present on the glass slides. If peptides are bound to the surface of the metals, blue staining by the CBB staining can be observed. As shown in FIG. 4, 39 slC was adhered to all of the metal plates.

The invention claimed is:

1. An adhesive molecule comprising the amino acid sequence of SEQ ID NO: 1, or the amino acid sequence of SEQ ID NO: 1 wherein at least one tyrosine is modified to dihydroxyphenylalanine.

2. The adhesive molecule according to claim 1, comprising the amino acid sequence of SEQ ID NO:1 wherein at least one tyrosine is modified to dihydroxyphenylalanine.

3. An adhesive comprising the adhesive molecule according to claim 1.

4. A polynucleotide having a nucleotide sequence encoding the adhesive molecule according to claim 1.

5. A vector comprising the polynucleotide according to claim 4.

6. A method of bonding a first object to a second object, comprising applying the adhesive according to claim 3 to a surface of the first object.

7. A method of coating a surface of an object comprising applying the adhesive according to claim 3 to the surface of the object.

8. A method of enhancing adherence of an adhesive molecule comprising reacting tyrosinase with the adhesive molecule according to claim 1.

9. An adhesive comprising the adhesive molecule according to claim 2.

10. A polynucleotide having a nucleotide sequence encoding the adhesive molecule according to claim 2.

11. A vector comprising the polynucleotide according to claim 10.

12. A method of bonding a first object to a second object, comprising applying the adhesive according to claim 9 to a surface of the first object.

13. A method of coating a surface of an object comprising applying the adhesive according to claim 9 to the surface of the object.

* * * * *

SEQUENCE LISTING

```
<160> NUMBER OF SEQ ID NOS: 2

<210> SEQ ID NO 1
<211> LENGTH: 18
<212> TYPE: PRT
<213> ORGANISM: Artificial Sequence
<220> FEATURE:
<223> OTHER INFORMATION: 39s1C

<400> SEQUENCE: 1

Asn Arg Val Asp Asn Tyr Lys Glu Val Tyr Asn Lys Ile Tyr Asn Lys
1               5                   10                  15

Arg Asn

<210> SEQ ID NO 2
<211> LENGTH: 69
<212> TYPE: DNA
<213> ORGANISM: Artificial Sequence
<220> FEATURE:
<223> OTHER INFORMATION: nucleotide sequence of 39s1C with restriction
      sites

<400> SEQUENCE: 2
ggatccaatc gtgttgataa ctataaagaa gtgtataaca agatttacaa caaacgcaat      60
taaggatcc                                                             69
```